United States Patent [19]

Schubert et al.

[11] 4,454,355
[45] Jun. 12, 1984

[54] PROCESS FOR THE PREPARATION OF P-NITROPHENETOLE

[75] Inventors: Hans Schubert, Kelkheim; Konrad Baessler, Frankfurt am Main, both of Fed. Rep. of Germany

[73] Assignee: Hoechst Aktiengesellschaft, Frankfurt am Main, Fed. Rep. of Germany

[21] Appl. No.: 381,217

[22] Filed: May 24, 1982

[30] Foreign Application Priority Data

May 26, 1981 [DE] Fed. Rep. of Germany ....... 3120912

[51] Int. Cl.$^3$ .................... C07C 76/02; C07C 79/35
[52] U.S. Cl. .................................................. 568/584
[58] Field of Search ........................................ 568/584

[56] References Cited

FOREIGN PATENT DOCUMENTS 1539183 1/1979 United Kingdom ............... 568/584

Primary Examiner—Bernard Helfin
Attorney, Agent, or Firm—Curtis, Morris & Safford

[57] ABSTRACT

The invention provides a process for the preparation of p-nitrophenetole with high yields and in an especially pure form from p-chloronitrobenzene and ethanol by heating to a temperature of from 60° to 80° C. with addition of alkali metal hydroxide and a phase transfer catalyst.

2 Claims, No Drawings

PROCESS FOR THE PREPARATION OF P-NITROPHENETOLE

It is known from British Patent Specification No. 1,539,183, that p-nitrophenetole can be prepared by reaction of p-chloronitrobenzene with sodium hydroxide solution in ethanol in the presence of a phase transfer catalyst. In this process 1.6 mols of ethanol and 3 mols of 50% sodium hydroxide per mol of p-chloronitrobenzene are reacted at 90° C., thus yielding the product with an about 90% yield and a melting point of 53°-57° C. As byproduct, about 10% of 4,4'-dichloroazoxybenzene are formed. The separation of this azoxybenzene requires much expenditure, and furthermore, the purity of the p-nitrophenetole is insufficient for most application fields, especially that of dyestuff intermediates.

It has now been found that p-nitrophenetole is obtained with excellent purity and high yields by reaction of p-chloronitrobenzene with ethanol and alkali metal hydroxide in the presence of a phase transfer catalyst, when the reaction is carried out at a temperature in the range of from 60° to 80° C. Thus, a product having a melting point of 58°-59.5° C. and being free from 4,4'-dichloroazoxybenzene, p-chloronitrobenzene, 4,4'-diethoxyazobenzene and p-nitrophenol is obtained with a yield of about 95%.

Preferred embodiments of the invention are described in detail as follows:

The alkali metal hydroxide, especially sodium hydroxide, is advantageously used as concentrated aqueous solution, especially in solid form as pellets, flakes, powder or prills, without formation of by-products, especially 4,4'-dichloroazoxybenzene, and without decrease of yield or deterioration of purity. Per mol of p-chloronitrobenzene from 1.1 to 3 mols of alkali metal hydroxide, especially 1.3 to 1.5 mols of solid sodium hydroxide, are used. When solid alkali metal hydroxide is employed, the amount of ethanol can be decreased, too, without risking that the p-chloronitrobenzene does not completely react and thus yield and purity are reduced. Thus, from 1.3 to 1.6 mols of ethanol are sufficient per mol of p-chloronitrobenzene when from 1.3 to 1.5 mols of solid sodium hydroxide are used.

The reaction temperature is preferably in the range of from 65° to 75° C., especially about 70° C.

As phase transfer catalysts, the usual products such as listed in British Patent Specification No. 1,539,183 may be used. Especially preferred is coconut alkaly-dimethylbenzyl-ammonium chloride which can be easily isolated from its commercial about 50% aqueous solution. By coconut alkyl there is to be understood a mixture of alkyl radicals having an even number of carbon atoms in the range of $C_{12}$-$C_{18}$, the $C_{12}$ amount being about 50%.

The following Examples illustrate the invention; parts and percentages being by weight unless otherwise stated.

EXAMPLE 1

A solution of 67 parts of coconut alkyl-dimethylbenzyl-ammonium chloride (obtained by distilling off water from 125 g of the commercial about 50% aqueous solution) in 388 parts of 95% ethanol was introduced into an apparatus fitted with a stirrer, 787.8 parts of p-chloronitrobenzene were added, and the batch was heated to 70° C. Subsequently, 1,600 parts of a 50% aqueous sodium hydroxide solution were added dropwise within 4 hours and with vigorous stirring, the temperature being maintained at 70° C. during the entire reaction time. After having added the NaOH, stirring was continued for 4 to 6 hours at this temperature, and then excess ethanol was distilled off from the reaction mixture under reduced pressure. The distillation sump was subsequently stirred twice at 70° C. with 1,000 parts each of water, the water phase was separated, the molten, organic phase was stirred in 1,500 parts of water until it was cold, the p-nitrophenetole was suction-filtered, and washed with 1 l of water, 1 l of about 1% hydrochloric acid, and 1 l of water, in this sequence.

Molar ratio: p-chloronitrobenzene:ethanol:NaOH=1:1.6:4.0.

Yield: 792 g=94.8% of th., relative to p-chloronitrobenzene.

S.P.: 57.8° C. (solidification point).

M.P.: 58° to 59.5° C.

Content of: 4,4'-dichlorazoxybenzene, <0.1%; p-chloronitrobenzene, <0.1%; 4,4'-diethoxy-azoxybenzene, <0.1%; p-nitrophenol, <0.1%.

COMPARATIVE EXAMPLE

According to Example 1, a solution of 67 parts of coconut alkyldimethylbenzyl-ammonium chloride in 388 parts of 95% ethanol was introduced into the vessel, and 787.8 parts of p-chloronitrobenzene were added, but the mixture was refluxed. Subsequently, 1,600 parts of 50% aqueous NaOH were added dropwise with vigorous stirring within 4 hours. After having stirred for a further 4 to 6 hours approximatively, excess ethanol was distilled off at a reduced pressure of about 350 mbar. Since the alkaline water phase could not be separated at 70° C. from the organic phase, the mixture was stirred until it was cold, and the solidified p-nitrophenetole was suction-filtered. The isolated p-nitrophenetole was then introduced twice into 1,000 parts of water each, heated to 70° C., stirred in the melt and then stirred until it was cold, subsequently suction-filtered, and washed with 1 l of water, 1 l of about 1% hydrochloric acid, and 1 l of water, in this sequence.

Molar ratio: p-chloronitrobenzene:ethanol:NaOH=1:1.6:4.0.

Yield: 747 g=89.4% of th., relative to p-chloronitrobenzene.

S.P.: could not be determined.

M.P.: 48° to 55° C.

Content of: 4,4'-dichlorazoxybenzene, abt. 13%; p-chloronitrobenzene, <0.1%; 4,4'-diethoxyazoxybenzene, abt. 10%; p-nitrophenol, abt. 2%; unknown substances, abt. 2%.

EXAMPLE 2

According to Example 1, a solution of 67 parts of coconut alkyldimethylbenzyl-ammonium chloride in 322.5 parts of 95% ethanol was introduced into the reactor, 787.8 parts of p-chloronitrobenzene were added, and the batch was heated to 70° C. Subsequently, 280 parts of sodium hydroxide (solid, in the form of prills) were constantly added within 4 hours and with vigorous stirring. The reaction temperature was not allowed to exceed 70° C. during the entire reaction time. After having added the sodium hydroxide, stirring was continued for 4 to 6 hours at 70° C. in order to complete the reaction. Work-up was as indicated in Example 1.

Molar ratio: p-chloronitrobenzene:ethanol:NaOH = 1:1.4:1.4.

Yield: 793 g=95.0 of th., relative to p-chloronitrobenzene.

S.P.: 57.8° C.

M.P.: 58° to 59.5° C.

Content of: 4,4'-dichlorazoxybenzene, <0.1%; p-chloronitrobenzene, <0.1%; 4,4'-diethoxy-azoxybenzene, <0.1%; p-nitrophenol, ≦0.1%.

What is claimed is:

1. In a process for the preparation of p-nitrophenetole wherein p-chloro nitro benzene and ethanol are heated with 1.1 to 3 mols of an alkali metal hydroxide per mol of p-chloro nitro benzene and in the presence of a phase transfer catalyst and in the absence of a solvent, the improvement consisting of carrying out the reaction at a temperature of from 65° to 75° C.

2. The process as claimed in claim 1, which comprises adding from 1.3 to 1.5 mols of sodium hydroxide per mol of p-chloronitrobenzene.

* * * * *